United States Patent
Bowden et al.

(10) Patent No.: US 9,642,651 B2
(45) Date of Patent: May 9, 2017

(54) INVERTED SERPENTINE SPINAL STABILITY DEVICE AND ASSOCIATED METHODS

(71) Applicant: Brigham Young University, Provo, UT (US)

(72) Inventors: Anton Bowden, Provo, UT (US); Larry Howell, Provo, UT (US); Todd Nelson, Provo, UT (US); Trevor Stephens, Provo, UT (US)

(73) Assignee: Brigham Young University, Provo, UT (US)

( * ) Notice: Subject to any disclaimer, the term of this patent is extended or adjusted under 35 U.S.C. 154(b) by 35 days.

(21) Appl. No.: 14/737,241

(22) Filed: Jun. 11, 2015

(65) Prior Publication Data

US 2016/0015428 A1 Jan. 21, 2016

Related U.S. Application Data

(60) Provisional application No. 62/011,343, filed on Jun. 12, 2014.

(51) Int. Cl.
*A61B 17/70* (2006.01)

(52) U.S. Cl.
CPC ........ *A61B 17/7026* (2013.01); *A61B 17/701* (2013.01); *A61B 17/7004* (2013.01); *A61B 17/7019* (2013.01); *A61B 17/7031* (2013.01)

(58) Field of Classification Search
CPC ............ A61B 17/7026; A61B 17/7019; A61B 17/7031; A61B 17/7004; A61B 17/701
See application file for complete search history.

(56) References Cited

U.S. PATENT DOCUMENTS

| | | |
|---|---|---|
| 3,945,053 A | 3/1976 | Hilberry et al. |
| 4,267,608 A | 5/1981 | Bora, Jr. |
| 5,405,408 A | 4/1995 | Pitkin |
| 5,415,661 A | 5/1995 | Holmes |
| 5,733,285 A | 3/1998 | Errico |
| 5,772,661 A | 6/1998 | Michelson |
| 5,964,760 A | 10/1999 | Richelsoph |
| 6,045,552 A | 4/2000 | Zucherman et al. |
| 6,355,040 B1 | 3/2002 | Richelsoph |
| 6,379,354 B1 | 4/2002 | Rogozinski |
| 6,440,169 B1 | 8/2002 | El berg |
| 6,527,804 B1 | 3/2003 | Gauchet et al. |

(Continued)

FOREIGN PATENT DOCUMENTS

| | | |
|---|---|---|
| KR | 10-2005-0080493 | 8/2005 |
| KR | 10-2006-0113318 | 11/2006 |

(Continued)

*Primary Examiner* — Ellen C Hammond
(74) *Attorney, Agent, or Firm* — Thorpe North & Western, LLP

(57) ABSTRACT

A spinal implant includes a plurality of frame segments that define a first frame array, the first frame array being coupled to a first mounting connection. A plurality of contiguous segments define a second frame array, the plurality of contiguous segments being coupled to a second mounting connection and being coupled to the first frame array. The first frame array and the second frame array are positioned relative to one another such that application of a force in a first direction to the first and second mounting connections results in application of a force in an opposing direction to the plurality of contiguous segments.

14 Claims, 15 Drawing Sheets

(56) References Cited

U.S. PATENT DOCUMENTS

| | | |
|---|---|---|
| 6,540,785 B1 | 4/2003 | Gill et al. |
| 6,572,653 B1 | 6/2003 | Simonson |
| 6,579,320 B1 | 6/2003 | Gauchet et al. |
| 6,610,093 B1 | 8/2003 | Pisharodi |
| 6,645,248 B2 | 11/2003 | Casutt |
| 6,723,127 B2 | 4/2004 | Ralph et al. |
| 6,793,678 B2 | 9/2004 | Hawkins |
| 6,802,867 B2 | 10/2004 | Manasas et al. |
| 6,811,567 B2 | 11/2004 | Reiley |
| 6,863,688 B2 | 3/2005 | Ralph et al. |
| 6,936,071 B1 | 8/2005 | Mamay et al. |
| 6,949,123 B2 | 9/2005 | Reiley |
| 6,964,666 B2 | 11/2005 | Jackson |
| 6,966,910 B2 | 11/2005 | Ritland |
| 6,974,478 B2 | 12/2005 | Reiley et al. |
| 6,983,924 B2 | 1/2006 | Howell et al. |
| 6,991,632 B2 | 1/2006 | Ritland |
| 6,997,955 B2 | 2/2006 | Zubok et al. |
| 7,029,475 B2 | 4/2006 | Panjabi |
| 7,074,238 B2 | 7/2006 | Stinson et al. |
| 7,093,827 B2 | 8/2006 | Culpepper |
| 7,115,129 B2 | 10/2006 | Heggeness |
| 7,144,369 B2 | 12/2006 | Shulzas |
| 7,207,992 B2 | 4/2007 | Ritland |
| 7,229,441 B2 | 6/2007 | Trieu et al. |
| 7,326,210 B2 | 2/2008 | Jahng et al. |
| 7,338,398 B2 | 3/2008 | Whiting et al. |
| 7,361,196 B2 | 4/2008 | Fallin et al. |
| 7,371,238 B2 | 5/2008 | Soboleski et al. |
| 7,377,942 B2 | 5/2008 | Berry |
| 7,445,635 B2 | 11/2008 | Fallin et al. |
| 7,458,981 B2 | 12/2008 | Fielding et al. |
| 7,476,238 B2 | 1/2009 | Panjabi |
| 7,476,251 B2 | 1/2009 | Zucherman et al. |
| 7,481,830 B2 | 1/2009 | Wall et al. |
| 7,485,133 B2 | 2/2009 | Cannon et al. |
| 7,485,134 B2 | 2/2009 | Simonson |
| 7,485,146 B1 | 2/2009 | Crook et al. |
| 7,491,218 B2 | 2/2009 | Amin et al. |
| 7,491,240 B1 | 2/2009 | Carver et al. |
| 7,494,507 B2 | 2/2009 | Dixon et al. |
| 7,537,615 B2 | 5/2009 | Lemaire |
| 7,618,441 B2 | 11/2009 | Groiso |
| 7,632,292 B2 | 12/2009 | Sengupta et al. |
| 7,682,375 B2 | 3/2010 | Ritland |
| 7,785,351 B2 | 8/2010 | Gordon et al. |
| 7,909,877 B2 | 3/2011 | Krueger et al. |
| 8,025,681 B2 | 9/2011 | Colleran et al. |
| 8,048,121 B2 | 11/2011 | Mitchell et al. |
| 8,080,038 B2 | 12/2011 | Bhatnagar et al. |
| 8,118,840 B2 | 2/2012 | Trieu et al. |
| 8,172,883 B2 | 5/2012 | Bowden et al. |
| 8,216,275 B2 | 7/2012 | Fielding et al. |
| 8,308,770 B2 | 11/2012 | Moumene et al. |
| 8,449,615 B2 | 5/2013 | Fleischmann |
| 8,663,284 B2 | 3/2014 | Beger et al. |
| 2002/0138077 A1 | 9/2002 | Ferree |
| 2003/0171751 A1 | 9/2003 | Ritland |
| 2004/0002708 A1 | 1/2004 | Ritland |
| 2004/0073215 A1 | 4/2004 | Carli |
| 2004/0176849 A1 | 9/2004 | Zubok et al. |
| 2005/0085814 A1 | 4/2005 | Sherman et al. |
| 2005/0101954 A1 | 5/2005 | Simonson |
| 2005/0113924 A1 | 5/2005 | Butterman |
| 2005/0113927 A1 | 5/2005 | Malek |
| 2005/0125065 A1 | 6/2005 | Zucherman et al. |
| 2005/0149023 A1 | 7/2005 | Ritland |
| 2005/0159818 A1 | 7/2005 | Blain |
| 2005/0165487 A1 | 7/2005 | Muhanna |
| 2005/0171543 A1 | 8/2005 | Timm et al. |
| 2005/0177156 A1 | 8/2005 | Timm et al. |
| 2005/0240270 A1 | 10/2005 | Zubok et al. |
| 2005/0261772 A1 | 11/2005 | Filippi et al. |
| 2006/0009768 A1 | 1/2006 | Ritland |
| 2006/0009850 A1 | 1/2006 | Frigg et al. |
| 2006/0036240 A1 | 2/2006 | Colleran |
| 2006/0041314 A1 | 2/2006 | Millard |
| 2006/0052784 A1 | 3/2006 | Dant et al. |
| 2006/0084987 A1 | 4/2006 | Kim |
| 2006/0184171 A1 | 8/2006 | Biederman et al. |
| 2006/0190079 A1 | 8/2006 | Istephano et al. |
| 2006/0206114 A1 | 9/2006 | Ensign et al. |
| 2006/0229608 A1 | 10/2006 | Foster et al. |
| 2006/0229609 A1 | 10/2006 | Wang |
| 2006/0240533 A1 | 10/2006 | Sengupta et al. |
| 2006/0271047 A1 | 11/2006 | Jackson |
| 2006/0271051 A1 | 11/2006 | Berrevoets |
| 2007/0016193 A1 | 1/2007 | Ritland |
| 2007/0028714 A1 | 2/2007 | Lusk et al. |
| 2007/0043365 A1 | 2/2007 | Ritland |
| 2007/0049936 A1 | 3/2007 | Colleran et al. |
| 2007/0088440 A1 | 4/2007 | Eisermann et al. |
| 2007/0179618 A1 | 8/2007 | Trieu et al. |
| 2007/0191832 A1 | 8/2007 | Trieu |
| 2007/0270836 A1 | 11/2007 | Bruneau et al. |
| 2008/0015588 A1 | 1/2008 | Hawkes |
| 2008/0077246 A1 | 3/2008 | Fehling et al. |
| 2008/0140075 A1 | 6/2008 | Ensign |
| 2008/0183209 A1 | 7/2008 | Robinson et al. |
| 2008/0195208 A1 | 8/2008 | Castellvi |
| 2008/0195213 A1 | 8/2008 | Halverson et al. |
| 2008/0312693 A1 | 12/2008 | Trautwein et al. |
| 2009/0005819 A1 | 1/2009 | Ben-Mokhtar et al. |
| 2009/0048631 A1 | 2/2009 | Bhatnagar et al. |
| 2009/0099608 A1 | 4/2009 | Szczesny |
| 2009/0228045 A1 | 9/2009 | Hayes et al. |
| 2009/0259257 A1 | 10/2009 | Prevost |
| 2009/0270921 A1 | 10/2009 | Krae |
| 2010/0204732 A1 | 8/2010 | Aschmann et al. |
| 2010/0211106 A1 | 8/2010 | Bowden et al. |
| 2010/0217324 A1 | 8/2010 | Bowden et al. |
| 2010/0217334 A1 | 8/2010 | Hawkes |
| 2010/0222821 A1 | 9/2010 | Bowden et al. |
| 2010/0222823 A1 | 9/2010 | Bowden et al. |
| 2010/0241232 A1 | 9/2010 | Halverson et al. |
| 2013/0150891 A1 | 6/2013 | Dodgen et al. |

FOREIGN PATENT DOCUMENTS

| | | |
|---|---|---|
| WO | WO 2004/071344 | 8/2004 |
| WO | WO 2005/051243 | 6/2005 |
| WO | WO 2005/107654 | 11/2005 |
| WO | WO 2006/127992 | 11/2006 |
| WO | WO 2008/070840 | 6/2008 |
| WO | WO 2008/100891 | 8/2008 |
| WO | WO 2010/096621 | 8/2010 |
| WO | WO 2010/096829 | 8/2010 |
| WO | WO 2010/108010 | 9/2010 |

Anterior ◄────┼────► Posterior

INVERTED SERPENTINE SPINAL STABILITY DEVICE AND ASSOCIATED METHODS

PRIORITY CLAIM

This application claims priority to and of U.S. Provisional Patent Application Ser. No. 62/011,343, filed Jun. 12, 2014, which is hereby incorporated herein by reference in its entirety.

RELATED CASES

This application is related to U.S. patent application Ser. No. 13/491,129, filed Jun. 7, 2012, which is hereby incorporated herein by reference.

FIELD OF THE INVENTION

Embodiments of the present invention relate generally to mechanical spinal implants and, more particularly, to dynamic spinal implants that: relieve symptoms of degenerative spinal diseases; that restore healthy motion to an unhealthy spine; and that promote the healing of spinal tissues.

BACKGROUND

The human spine functions through a complex interaction of several parts of the anatomy. FIGS. 1 and 2 (the cross-section A-A of FIG. 1) illustrate a segment of the spine 4, with vertebra 5. The vertebra 5 include the vertebral body 6, the spinous process 8, transverse process 10, pedicle 12, and laminae 14. A functional spine, comprising several vertebra 5, typically subcategorized as being part of the cervical, thoracic, lumbar, sacral, and coccygeal regions as known, provides support to the head, neck, trunk, and transfer weight to lower limbs, protects the spinal cord 20, from which peripheral nerves 32 extend, and maintain the body in an upright position while sitting or standing.

Also illustrated in FIGS. 1 and 2, the spinal segment 4 includes intervertebral discs 20 that separate adjacent vertebra 5. The intervertebral discs 20 provide motion, load bearing and cushioning between adjacent vertebrae 5. Intervertebral discs 20 are the largest avascular structure in the body, relying on diffusion for its nutrition. The diffusion of nutrients is aided by the compression cycles that the intervertebral discs 20 undergo during the course of normal movement, which drives out waste products and cycles fluids. Lying down and resting reduces the load on the intervertebral discs 20 allowing nutrients to diffuse into the intervertebral discs 20.

Also illustrated in FIGS. 1 and 2, the spinal segment includes spinal facet joints 16. Spinal facet joints 16 join the adjacent vertebrae 6. The spinal facet joints 16 are synovial joints that function much like those of the fingers. Together with the intervertebral disc 20, the spinal facet joints 16 function to provide proper motion and stability to a spinal segment 4. Thus, each spinal segment 4 includes three joints: the intervertebral disc 20 in the anterior aspect of the spinal segment 4 and the two spinal facet joints 16 in the posterior aspect of the spinal segment 4.

For the spinal segment 4 to be healthy, each of the intervertebral disc 20 and the spinal facet joints 16 must be healthy. To remain healthy these joints require motion. The intervertebral disc 20 and the spinal facet joints 16 function together to provide both quality and quantity of motion. The quality of the motion is exhibited by the non-linear energy storage (force-deflection, torque-rotation) behavior of the spinal segment 4. The quantity of motion is the range of segmental rotation and translation.

Back pain due to diseased, damaged, and/or degraded intervertebral discs 20 and/or spinal facet joints 16 is a significant health problem in the United States and globally. A non-exhaustive and non-limiting illustration of examples of diseased and/or damaged intervertebral discs are shown in FIG. 3. While a healthy intervertebral disc 20 is illustrated at the top of the spine segment 18, diseased and/or damaged discs are also illustrated. The diseased and/or damaged discs include a degenerated disc 22, a bulging disc 24, a herniated disc 25, a thinning disc 26, discs indicating symptoms of degeneration with osteophyte formation 28, as well as hypertrophic spinal facets 29.

A degenerating spinal segment 18 is believed to be the product of adverse changes to its biochemistry and biomechanics. These adverse changes create a degenerative cascade affecting the quality and/or quantity of motion and may ultimately lead to pain. For example, as the health of a spinal segment 18 degenerates and/or changes, the space through which the spinal cord 30 and peripheral nerves 32 (FIGS. 1 and 2) pass can become constricted and thereby impinge a nerve, causing pain. For example, the spinal cord 30 or peripheral nerves 32 may be contacted by a bulging disc 24 or herniated disc 25 or hypertrophic spinal facet 29 as illustrated in FIG. 3. As another example, a change in the spinal segment 18, such as by a thinning disc 26 may alter the way in which the disc functions, such that the disc and spinal facets may not provide the stability or motion required to reduce muscle, ligament, and tendon strain. In other words, the muscular system is required to compensate for the structural deficiency and/or instability of the diseased spinal segment 18, resulting in muscle fatigue, tissue strain, and hypertrophy of the spinal facets, further causing back pain. The pain this causes often leads patients to limit the pain-causing motion; but this limited motion, while offering temporary relief, may result in longer-term harm. because the lack of motion limits the ability of the disc to expel waste and obtain nutrients as discussed above.

Of course, other diseases of the disc and other back related problems and/or maladies afflict many people. For example, as the disc degenerates the spinal facet joints undergo a change in motion and in loading. This causes the spinal facet joints to begin to degenerate. Spinal facet joint arthritis is an additional source of pain. Also, scoliosis, or a lateral curvature of the spine, is illustrated in FIG. 4. A patient's body 40 is illustrated in outline. Also illustrated is the lateral curvature of a scoliotic spine 42 that is afflicted with scoliosis. The scoliotic center line 44 of the scoliotic spine 42 is illustrated, as compared to a healthy centerline or axis 46 of a healthy spinal column or functional spine unit. Conditions such as kyphosis, an exaggerated outward-posterior curvature of the thoracic region of the spine resulting in a rounded upper back, lordosis, an exaggerated forward curvature of the lumbar and cervical regions of the spine, and other conditions also afflict some patients.

In many instances of degenerative disc disease, fusion of the vertebrae is the standard of care for surgical treatment, illustrated in FIG. 5. In the U.S. alone, approximately 349,000 spinal fusions are performed each year at an estimated cost of $20.2 billion. The number of lower back, or lumbar, fusions performed in the U.S. is expected to grow to approximately 5 million annually by the year 2030 as the population ages, an increase of 2,200%.

Spinal fusion aims to limit the movement of the vertebra that are unstable or causing a patient pain and/or other symptoms. Spinal fusion typically involves the removal of a diseased disc 50, illustrated in outline in FIG. 5. The removed disc 50 is replaced by one or more fusion cages 52, which are filled or surrounded by autograft bone that typically is harvested by excising one or more spinal facet joints 57. Vertebral bodies 51 adjacent the removed disc 50 are stabilized with one or more posterior supports 58 that are fixedly connected to the vertebral bodies 51 with the use of pedicle screws 54 that are screwed—such as by use of a bolt-style head 56 to turn the pedicle screw 54—into a hole drilled into the pedicle 12 of the vertebral bodies 51.

Fusion, however, often fails to provide adequate or sufficient long-term relief in about one-half of the treatments, resulting in low patient satisfaction. Further, fusion, by definition, restricts the overall motion of the treated functional spine unit, imposing increased stresses and range of motion on those portions of the spinal segment adjacent to the fused vertebral bodies 51. Fusion of a spinal segment has been indicated as a potential cause of degeneration to segments adjacent to the fusion. The adjacent spinal facet joints 57 and adjacent discs 59 often have to bear a greater load as a result of the fusion than would typically be the case, leading to possible overloading and, in turn, degeneration. Thus, surgical fusion often provides short-term relief, but possibly greater long-term spinal degradation than would otherwise have occurred.

Thus, a challenge to alleviating the back pain associated with various ailments is to find a remedy that, ideally, does not involve removing the diseased disc or damaging the spinal facet joints, and that provides sufficient stability to the diseased segment to alleviate pain and/or other symptoms, while still providing sufficient freedom of movement to allow the disc and spinal facet joints to return to health.

A further challenge is simply the complex, multi-dimensional nature of movement associated with a functional spine unit. Illustrated in FIG. 6 are the varying, orthogonal axes around which a functional spine unit moves. For example, a vertebra 5 is illustrated with an X-axis 60, around which a forward bending motion, or flexion, 61 in the anterior direction occurs. Flexion 61 is the motion that occurs when a person bends forward, for example. A rearward bending motion, or extension, 62 is also illustrated. The Y-axis 63 is the axis around which lateral extension, or bending, 64, left and right, occurs. The Z-axis 65 is the axis around which axial rotation 66, left and right, occurs. Spinal fusion, as discussed above, limits or prevents flexion 61-extension 62, but also limits or prevents motion in lateral extension, or bending, 64 and axial rotation 66. Thus, an improved alternative remedy to fusion preferably allows for movement with improved stability around each of the three axes, 60, 63, and 65.

Another difficulty associated with the complex motion of the spine is that the center-of-rotation for movement around each of the X-axis 60, Y-axis 63, and Z-axis 65 differs for each axis. This is illustrated in FIG. 7, in which the center-of-rotation for the flexion 61-extension 62 motion around the X-axis 60 is located at flexion-extension center-of-rotation 70. The center-of-rotation for the lateral extension, or bending, 64 motion around the Y-axis 63 is located at lateral extension, or bending, center-of-rotation 73. The center-of-rotation for the axial rotation 66 around the Z-axis 65 is located at axial rotation center-of-rotation 75. For more complex motion patterns (e.g., combined flexion, lateral extension/bending, etc.) a two-dimensional representation of the center-of-rotation is inadequate, but the three-dimensional equivalent called the helical axis of motion, or instantaneous screw axis can be employed. Spinal remedies which force rotation of a spinal segment around any axis other than the natural helical axis impose additional stresses on the tissue structures at both the diseased spinal segments and the adjacent spinal segments. Compounding the issue for the centers-of-rotation is that they actually change location during the movement, i.e., the location of the centers-of-rotation are instantaneous. Thus, a preferable remedy to spinal problems would account for the different instantaneous centers-of-rotation throughout the range of motion. Stated differently, a preferable remedy to spinal problems would allow the diseased spinal segment and adjacent spinal segments to under motion approximate that of the natural helical axis through the range of motions.

Many previous efforts have been made to solve at least some of the problems associated with spinal fusion, but with varying degrees of success. For example, U.S. Pat. No. 7,632,292 (the '292 Patent) to Sengupta and Mulholland, discloses an arched-shaped spring mechanism that is attached to adjacent vertebrae via pedicle screws. This device relies on the extension and compression of the spring to accommodate flexion 61 and extension 62 about the X-axis 60 illustrated in FIG. 6. The device disclosed in the '292 Patent addresses only flexion-extension and neither lateral extension/bending nor axial rotation, which would both still be improperly supported. Further, the '292 Patent does not account for the instantaneous centers-of-rotation; in other words, the centers-of-rotation will be misplaced for motions other than flexion. In addition, it may be anticipated that the device is either too stiff to provide proper motion or that the extension-compression cycles may lead to fatigue failure of the device.

Another example is U.S. Pat. No. 6,966,910 (the '910 Patent) and its associated family of applications to Ritland. As with the '292 Patent, the '910 Patent relies on the extension-compression cycle of a spring mechanism—specifically the reverse curves within the mechanism—to accommodate flexion 61 and extension 62 about the X-axis 60 illustrated in FIG. 6. Lateral extension/bending and axial rotation are not addressed.

SUMMARY

In accordance with one aspect of the invention, a spinal implant is provided, including a plurality of frame segments that define a first frame array, said first frame array being coupled to a first mounting connection. A plurality of contiguous segments define a second frame array, said plurality of contiguous segments being coupled to a second mounting connection and being coupled to the first frame array. The first frame array and the second frame array are positioned relative to one another such that application of a force in a first direction to the first and second mounting connections results in application of a force in an opposing direction to the plurality of contiguous segments.

In accordance with another aspect of the invention, a method of treating a spine with a spinal implant is provided, the method including: coupling a first mounting connection to a portion of the spine, the first mounting connection having a first frame array coupled thereto, the first frame array formed by a plurality of frame segments; and coupling a second mounting connection to another portion of the spine, the second mounting connection having a second frame array coupled thereto, the second frame array formed by a plurality of contiguous segments; and positioning the first frame array and the second frame array relative to one another such that application of a force in a first direction to the first and second mounting connections results in application of a force in an opposing direction to the plurality of contiguous segments.

Additional advantages of the present invention will become readily apparent from the following discussion, particularly when taken together with the accompanying drawings.

BRIEF DESCRIPTION OF THE DRAWINGS

To further clarify the above and other advantages and features of the one or more present inventions, reference to specific embodiments thereof are illustrated in the appended drawings. The drawings depict only exemplary embodiments and are therefore not to be considered limiting. One or more embodiments will be described and explained with additional specificity and detail through the use of the accompanying drawings in which.

Figure 1:
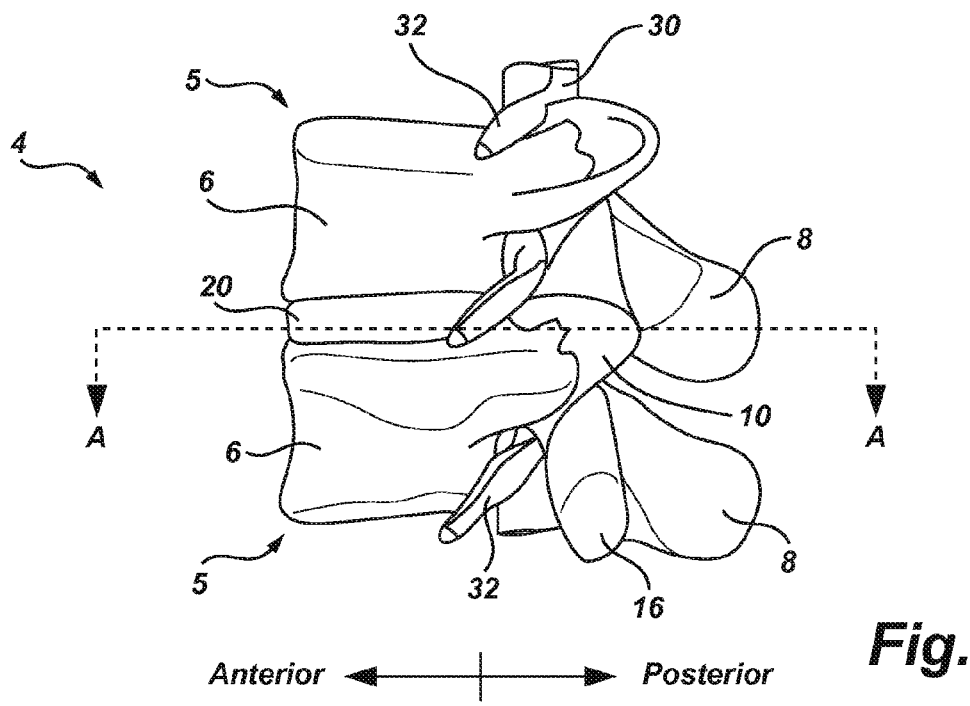
FIG. 1 is a segment of a functional spine unit.
Figure 2:
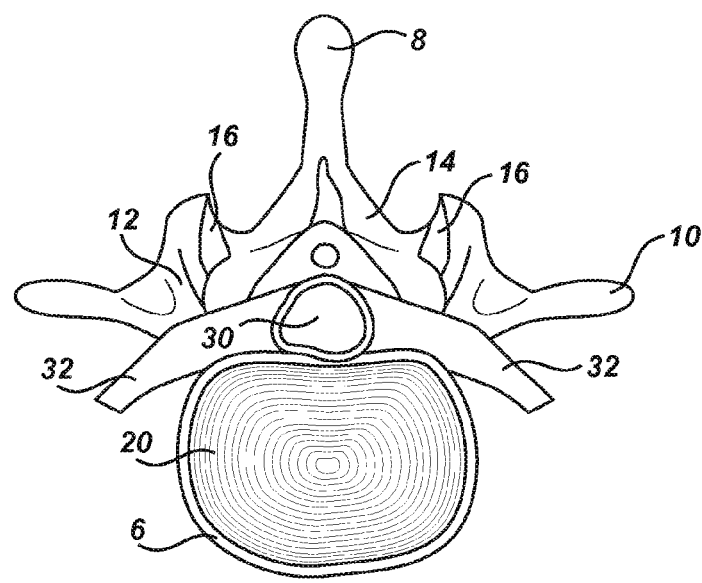
FIG. 2 is a cross-section of the segment of the functional spine unit illustrated in FIG. 1, taken along section A-A of FIG. 1.
Figure 3:
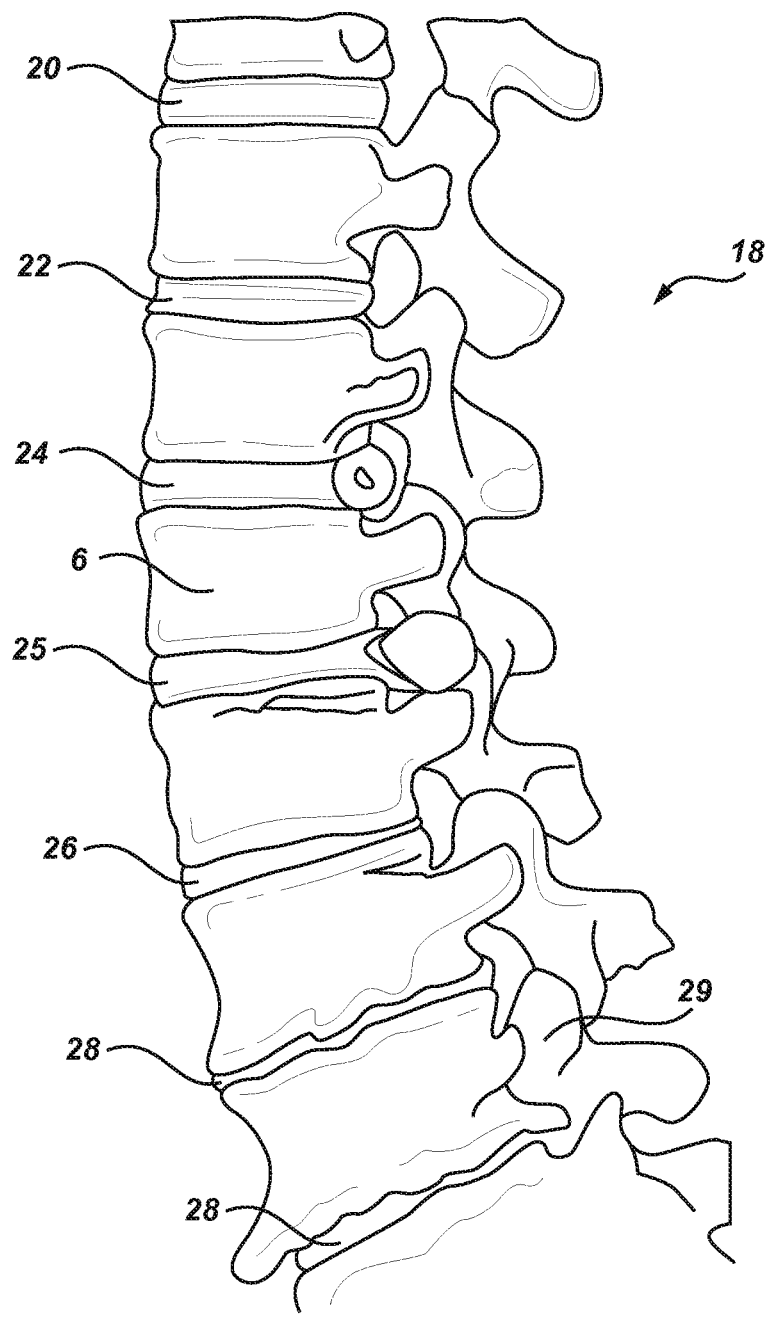
FIG. 3 is a segment of a spine illustrating various pathologies of intervertebral discs.

The drawings are not necessarily to scale.

DETAILED DESCRIPTION

Before the present invention is disclosed and described, it is to be understood that this invention is not limited to the particular structures, process steps, or materials disclosed herein, but is extended to equivalents thereof as would be recognized by those of ordinarily skilled in the relevant arts. It should also be understood that terminology employed herein is used for the purpose of describing particular embodiments only and is not intended to be limiting.

It must be noted that, as used in this specification and the appended claims, the singular forms "a" and "the" can include plural referents, unless the context clearly dictates otherwise. Thus, for example, reference to a "container" can include reference to one or more of such containers.

Definitions

In describing and claiming the present invention, the following terminology will be used.

As used herein, the term "ribbon" is to be understood to refer to a component (or a material forming a component) that has a thickness that is much smaller than its width. In one example, the thickness of the ribbon is at least four times smaller than is its width.

As used herein, relative terms, such as "upper," "lower," "upwardly," "downwardly," "vertically," etc., are used to refer to various components, and orientations of components, of the systems discussed herein, and related structures with which the present systems can be utilized, as those terms would be readily understood by one of ordinary skill in the relevant art. It is to be understood that such terms are not intended to limit the present invention but are used to aid in describing the components of the present systems, and related structures generally, in the most straightforward manner.

As used herein, the term "substantially" refers to the complete or nearly complete extent or degree of an action, characteristic, property, state, structure, item, or result. As an arbitrary example, when an object or group of objects is/are referred to as being "substantially" symmetrical, it is to be understood that the object or objects are either completely symmetrical or are nearly completely symmetrical. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As an arbitrary example, an opening that is "substantially free of" material would either completely lack material, or so nearly completely lack material that the effect would be the same as if it completely lacked material. In other words, an opening that is "substantially free of" material may still actually contain some such material as long as there is no measurable effect as a result thereof.

As used herein, the term "about" is used to provide flexibility to a numerical range endpoint by providing that a given value may be "a little above" or "a little below" the endpoint.

Directional terms, such as "upper," "lower," "inward," "distal," "proximal," etc., are used herein to more accurately describe the various features of the invention. Unless otherwise indicated, such terms are not used to in any way limit the invention, but to provide a disclosure that one of ordinary skill in the art would readily understand. Thus, while a component may be referenced as a "lower" component, that component may actually be above other components when the implant is installed within a patient. The "lower" terminology may be used to simplify the discussion of various figures.

Distances, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 inch to about 5 inches" should be interpreted to include not only the explicitly recited values of about 1 inch to about 5 inches, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value and should apply regardless of the breadth of the range or the characteristics being described.

Invention

As noted above, the kinetics and kinematics of the spine are quite complex, involving three separate axes around which motion occurs and three separate centers-of-rotation for the different motions. Applicants have recognized that previous spinal implants often address just one form of motion, typically flexion and extension, often through the use of springs of some type that flex and compress. Efforts to address more than one mode of rotation or motion typically tend to be complex, large, and often do not address each individual motion as effectively as devices dedicated to a single motion.

Through significant experimentation and engineering work, Applicants have discovered geometries that rely, in part, on the concept of torsion, rather than primarily compression and extension of springs, to provide a seemingly simple, yet decidedly complex, geometry that accommodates motion and stiffness around the three axis and accommodates the separate centers-of-rotation for each motion (flexion-extension, lateral extension or bending, and axial rotation). A compliant mechanism gains its motion from the deflection of flexible, resilient members. Such devices move without the aid of traditional sliding joints and bearings, thus increasing precision and eliminating friction and wear. They also integrate spring and hinge functions, allowing for the design of desired force-deflection behavior.

Figure 8:
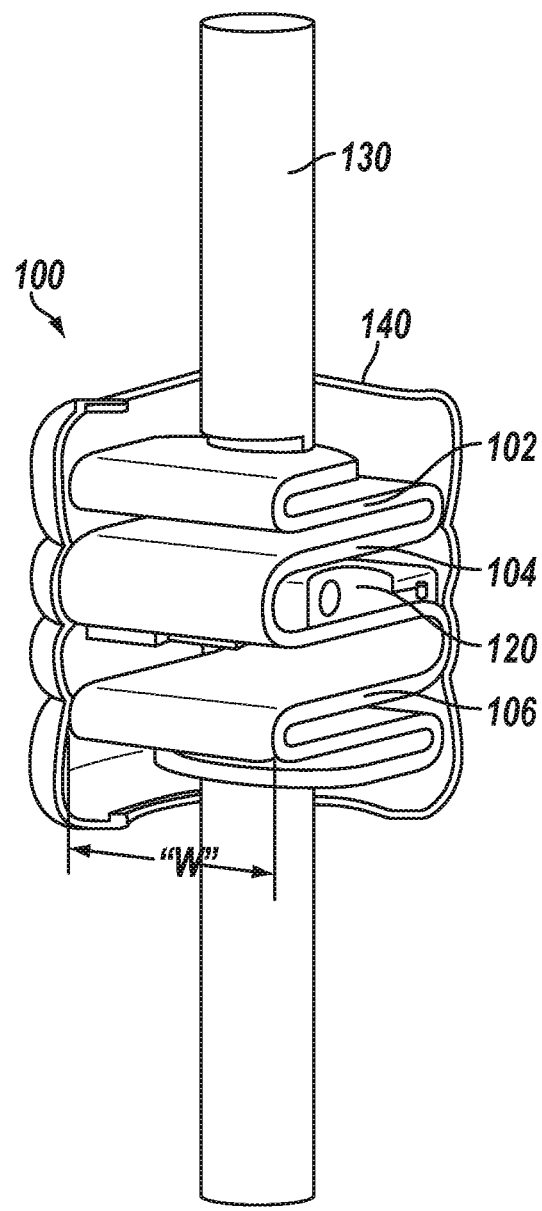
FIG. 8 illustrates an embodiment of an unimplanted compliant dynamic spinal implant, shown from the rear/posterior view, i.e., as it would appear from the rear of a person when implanted.
Figure 9:
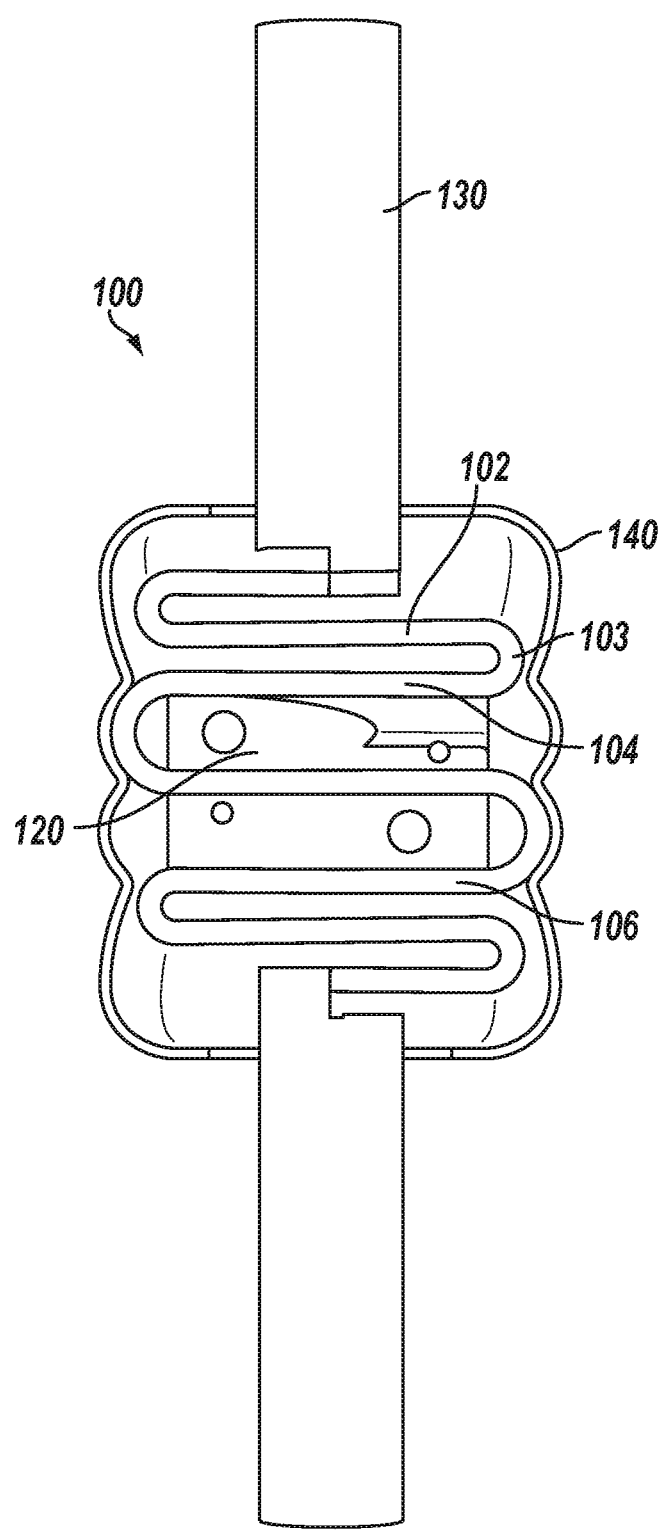
FIG. 9 is a lateral/side view of the spinal implant shown in FIG. 8.

An embodiment of a compliant dynamic spinal implant 100 is illustrated in FIGS. 8 and 9, which is an embodiment of a geometry that accomplishes, in part, the objectives provided above. A posterior view of the spinal implant 100 is presented in FIG. 8—reference being made to the direction the spinal implant would be viewed from when implanted in a patient. In other words, the spinal implant 100 in FIG. 8 appears as it would as viewed it from the patient's back. A lateral, or side, view, of the implant is presented in FIG. 9. It will be understood that while these references to view are presented for clarity, it should be understood the spinal implants 100 shown in FIGS. 8 and 9 appear in their unstressed, pre-implant condition, as will be explained in further detail below.

In this particular embodiment, the spinal implant 100 comprises a plurality of contiguous segments. In one embodiment, these contiguous segments define a segment array that includes segments (which include, but are not limited to, 102, 104, 106, etc.) that extend from a first side of the segment array to a second side of the segment array in an overlapping configuration. The segments are operable to apply a torque to a degenerate spinal segment in each of three orthogonal axes. The implant can include at least one mounting connection 130 configured to connect said spinal implant to a mounting mechanism. Such mounting mechanism (one shown by example at 202 in FIG. 11 as a pedicle screw) can be configured to attach the spinal implant to a degenerate spinal segment. While not so required, in one aspect of the invention, the segment array is substantially centered between two mounting mechanisms.

The array of segments 102, 104, 106, etc., are arranged in a generally serpentine orientation and provide many of the advantages of conventional spinal implants in much more compact package size. For example, in one embodiment of the invention, the overall volume consumed by the array is as small as 12×12×15 mm while providing a 100 N reaction force at 2 mm of deflection. Such package size is much smaller than can be achieved by functional spinal implants found in the prior art.

The segments 102, 104, 106, etc., are generally each joined by a continuously curving end segment (e.g., 103 in FIG. 9) that transitions from one segment (102) to an adjacent, overlapping segment (104). The continuous, serpentine material aids in providing smooth force response to loads applied to the implant, while minimizing the size requirement of the implant. In one aspect of the invention, a continuous ribbon of material alternately and contiguously extends from one side of the array to another side of the array in an overlapping configuration. The size and shape of the various segments of the array are discussed in further detail below, in conjunction with FIG. 15.

In accordance with one aspect of the invention, an insert (120 in FIGS. 8 and 9) can be positioned between two of the segments of the segment array. The insert can be operable to alter a force-deflection characteristic of the spinal implant. In the example shown (probably best appreciated in FIG. 9), the insert includes a generally curvilinear surface along which segment 104 is forced to track as the implant is compressed. One of ordinary skill in the art, having possession of this disclosure, will readily appreciate that constraining the bending of segment 104 along the surface of the insert 120 will alter the force-deflection response of the segment, and thereby the force-deflection response of the implant. While the insert shown will perform primarily as the implant compresses, inserts can also be inserted that alter the force-deflection characteristics of the spinal implant as it expands (e.g., as a tensile force is applied to the implant).

The shape and size of the insert 120 can be varied to achieve a desired force-deflection response from the implant 100 that can be tailored to treat a specific patient for a specific condition. The discussion relating to FIGS. 12, 13 and 14 addresses this aspect of the invention in greater detail.

Figure 10:
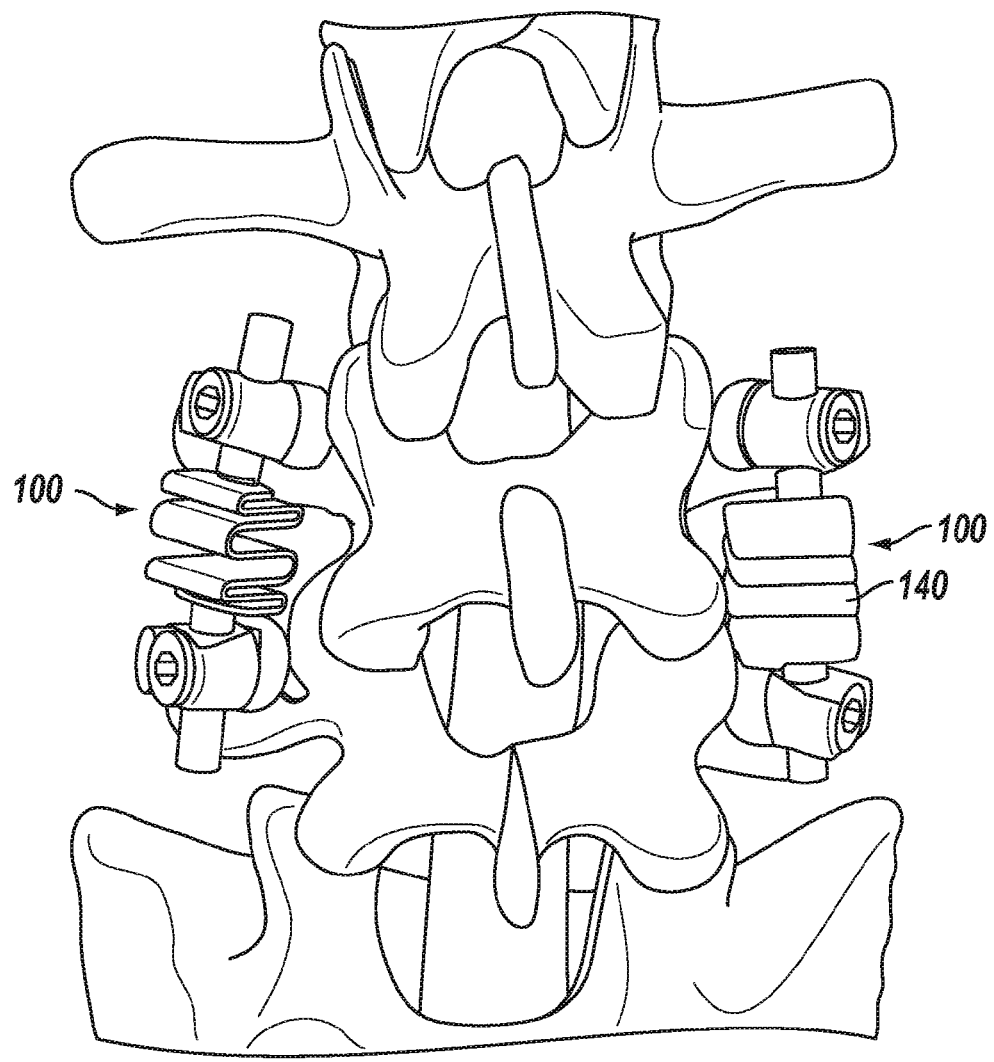
FIG. 10 shows embodiments of the spinal implant as they would appear implanted in a pair of lumbar vertebrae as viewed from the rear.

As shown in FIGS. 8 through 10, in one embodiment, a protective shroud 140 can be provided. The shroud 140 can be fittable about the spinal implant 100 and can aid in limiting or preventing surrounding tissue from contacting the spinal implant. The shroud can be formed from a variety of materials, including biocompatible polymers and the like. As best seen in FIG. 8, the shroud can generally fit about the mounting connections 130 and can be formed in two parts that can be friction-pressed together after installation of the implant 100. Alternately, the shroud can be formed about the implant prior to installation.

The shroud 140 can also provide a manner by which the insert 120 can be maintained in position within the segments 102, 104, etc. of the implant 100. By coupling the insert to the shroud, the insert need not necessarily be attached to any portion of the implant, but will still be maintained in proper position relative to the implant.

The spinal implant 100 optionally includes at least one mounting connection (130 in FIGS. 8 and 9, for example) for connecting the spinal implant 100 to a mounting mechanism. For example, an embodiment of a mounting connection includes through holes, through which a mounting mechanism, typically, although not necessarily, a pedicle screw, is positioned to hold the spinal implant in position in the patient—i.e., the mounting mechanism attaches the spinal implant 100 to at least a portion of a spinal segment, such as a vertebra, a pedicle, or other bony structure of a patient as will be discussed below. Of course, pedicle screws are merely one example of a mounting mechanism for attaching the spinal implant 100 to a patient's vertebrae. Other mounting mechanisms, such as the use of pins, biocompatible adhesives, straps, and the like, fall within the scope of this disclosure.

The spinal implant 100 can be formed of biocompatible plastics, polymers, metals, metal alloys, laminates, shape-memory materials, and other similar materials, either wholly as one material or as a combination of materials—i.e., different segments may be manufactured from different materials. Optionally, embodiments of the spinal implant can be made from bioabsorbable materials that a patient's body will naturally breakdown over time, thus potentially avoiding the need for a second surgery to remove the spinal implant 100, should such an option prove necessary and/or desirable.

An embodiment of the spinal implant 100 can optionally be made with nitinol, a metal alloy of nickel and titanium, that provides the ability of shape-memory. A spinal implant 100 made from such materials would be manufactured into a first shape or geometry or configuration having a known and desired first torque response. The spinal implant 100 would then be manipulated into a second shape or geometry having a known and desired second torque response. The spinal implant 100, in the second shape or geometry or configuration, then would be implanted in the patient. After implantation, a physician can apply an activating agent, such as heat, current, or other parameter, to cause the spinal implant 100 to revert back to its original, first shape or geometry, allowing the material to consequently revert to its first torque response. Thus, a measure of adjustability in the torque response of the spinal implant 100—even post-surgery—can be manufactured into the spinal implant 100. For example, in the case of nitinol, applying a parameter such as heat to the spinal implant and, in so doing, raising the spinal implant to a temperature above the transition temperature of the nitinol causes the spinal implant to revert to its first shape or geometry. In so doing, the stiffness of the spinal implant could be altered by, for example, making the spinal implant significantly stiffer so that it approximates more closely the stiffness provided by a spinal fusion procedure.

Another embodiment of the spinal implant 100 can be made from bioabsorbable materials, as mentioned. The patient's body would slowly absorb the spinal implant 100 and, in the process of so doing, the compressive load or force and torque provided or born by the spinal implant 100 would slowly be transferred to the intervertebral discs and/or vertebrae of the patient as the patient's spine healed and/or improved in health and strength. Thus, a bioabsorbable device contemplates and allows for a patient to regain his or her spinal health, an adjustment and transfer of force and torque from the spinal implant to the patient's body, and the eventual removal of the spinal implant through absorption rather than surgery.

While the various segments are typically shown as a continuous, or contiguous, unit, the various segments 102, 104, 106, etc., can be joined to one another. When the term "joined" is used herein, it is understood that the segments may be temporarily joined, through a removable connection, such as bolts, screws, biocompatible adhesives, and the like. Alternatively, one or more of the segments may be joined permanently, such as through the use of biocompatible epoxies, polymers, and other known methods of joining the segments. In yet another embodiment, the individual segments may be formed as a single, unitary piece, such as by laminating, molding, pressing, stamping, milling, and other known methods.

An advantage of embodiments of the spinal implants disclosed—provided that they are manufactured as single, unitary piece—is that they do not have any joints or surfaces that might rub or wear against each other because the embodiments rely on deflection of the segment(s) to provide a force and/or torque. The relative lack of rubbing or movement against other elements as compared to prior art devices minimizes or prevents the formation of wear particles that might otherwise be generated. This is the case for those prior art devices that have biocompatible surfaces that might wear off to expose non-biocompatible surfaces or, in some instances, the wear causes the biocompatible surface to become non-biocompatible, leading to additional wearing of the prior art devices at an accelerated rate.

Figure 11:
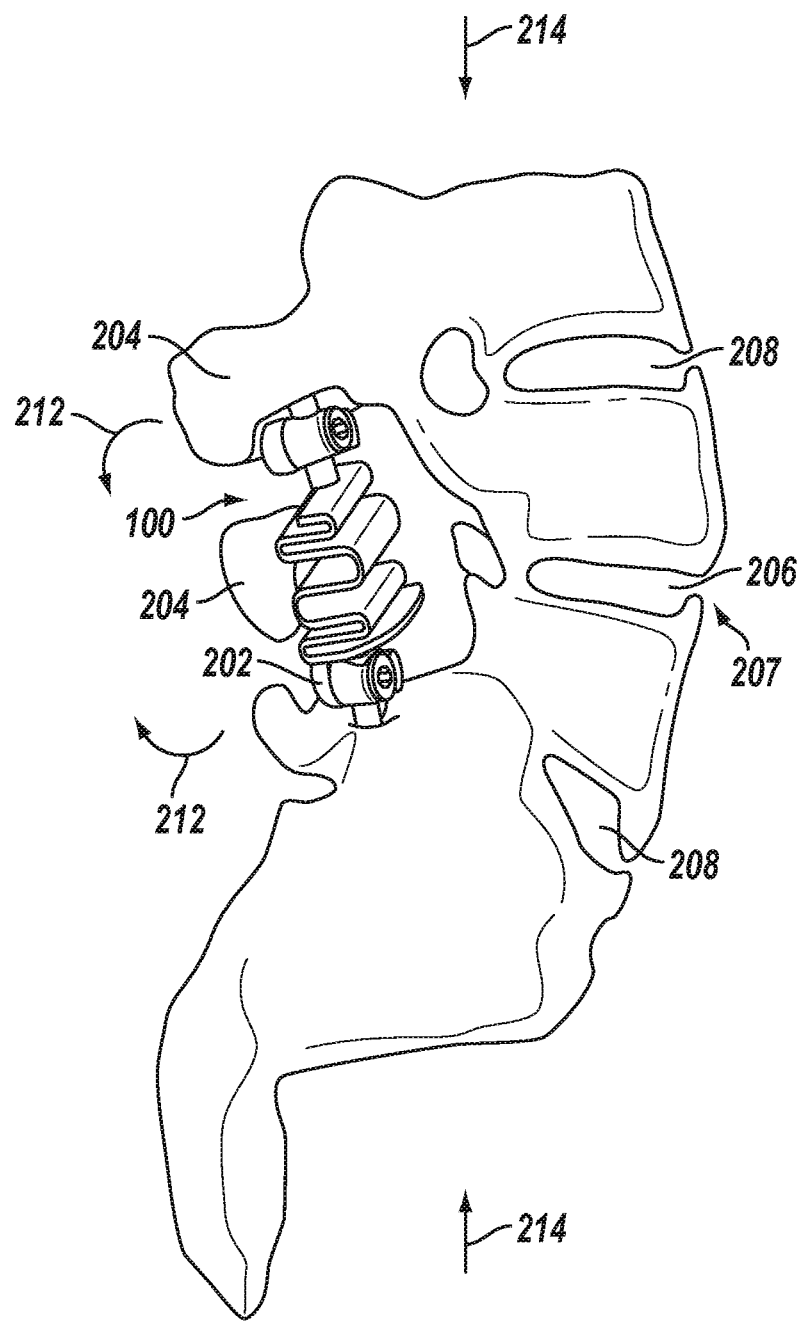
FIG. 11 is a lateral view of the spinal implant of FIG. 10 undergoing a compressive load and a torsional load.

For context, FIG. 10 generally, and FIG. 11 specifically, illustrate embodiments of the spinal implants 100 as they might appear implanted on a lumbar portion of the spine of a patient. As shown in FIG. 11, the spinal implants 100 are fixed to the vertebrae 204 adjacent to a diseased disc 206. In this embodiment, pedicle screws 202 are used to fix the spinal implants 200 to the vertebrae 204. (The method of surgical implantation will be discussed in more detail below.) Once implanted, the spinal implants 100 optionally provide an extension force, if they are prestressed, as will be discussed below, to help distract the vertebrae 204 from the diseased disc 206. Alternatively, the spinal implants 100 resist a compressive force 214 from the normal action of gravity upon the person, thus supporting a portion of the load that would otherwise have been born by the diseased disc 206. In addition, the spinal implants provide a torque 212 (about an axis perpendicular to the page of FIG. 11) that distracts the diseased disc 206 and, preferably, distracts an anterior portion 207 of the diseased disc 206. The torque 212 applied by the spinal implants 100 can be selected and adjusted to compensate at least partially and, preferably, almost fully, for the diseased disc 206, as will be explained further below.

A benefit of embodiments of the spinal implant is that they can be individually adjusted to a specific patient and that patient's pathologies, rather than relying on prior art devices that were manufactured for a predetermined subset of the population. The disadvantages of the latter approach are that it is rare that an individual patient's pathologies, by coincidence, are an exact match for a device. Thus, the patient must compromise, to a greater or lesser extent, on the performance and the relief that may be obtained through the use of some prior art devices. The implants can be tailored to provide a preferred, or "target" or "treatment" response to a particular patient's spinal condition. For example, the torque applied in any of the three axes of rotation can match that of a healthy spine (if that is the target treatment for the particular patient), or can overcompensate (e.g., apply a greater torque than a healthy spine would experience) when attempting to correct for some misalignment in the spine.

Figure 6:
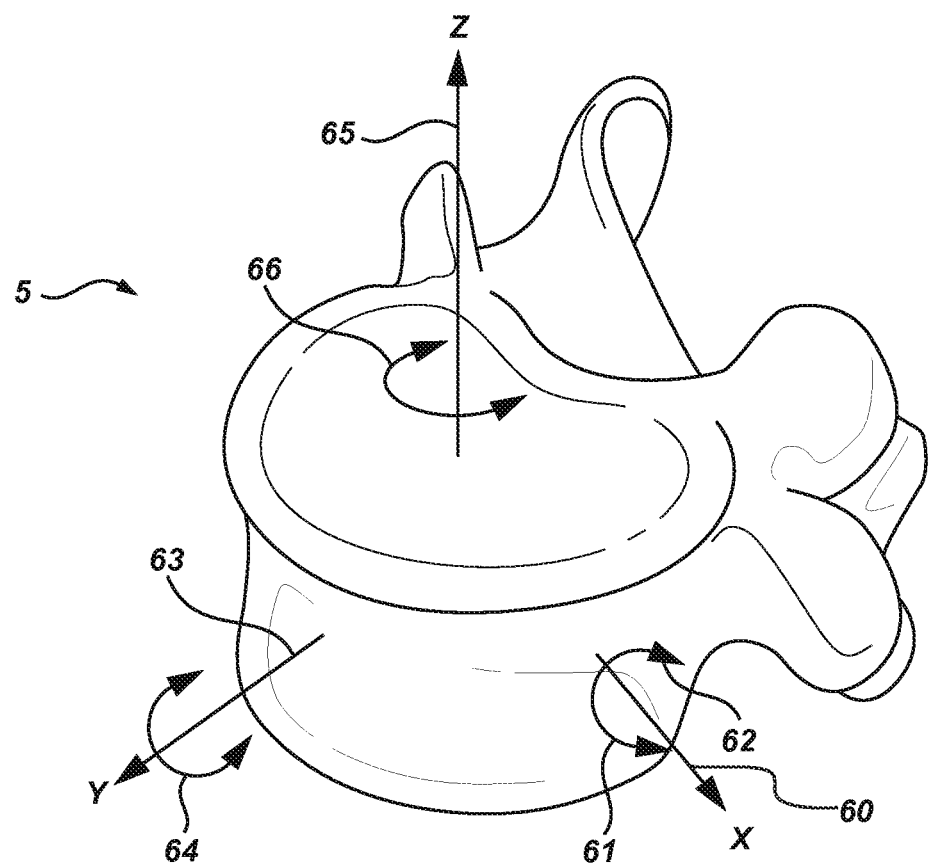
FIG. 6 illustrates the three axes of motion around which functional spine unit moves.
Figure 7:
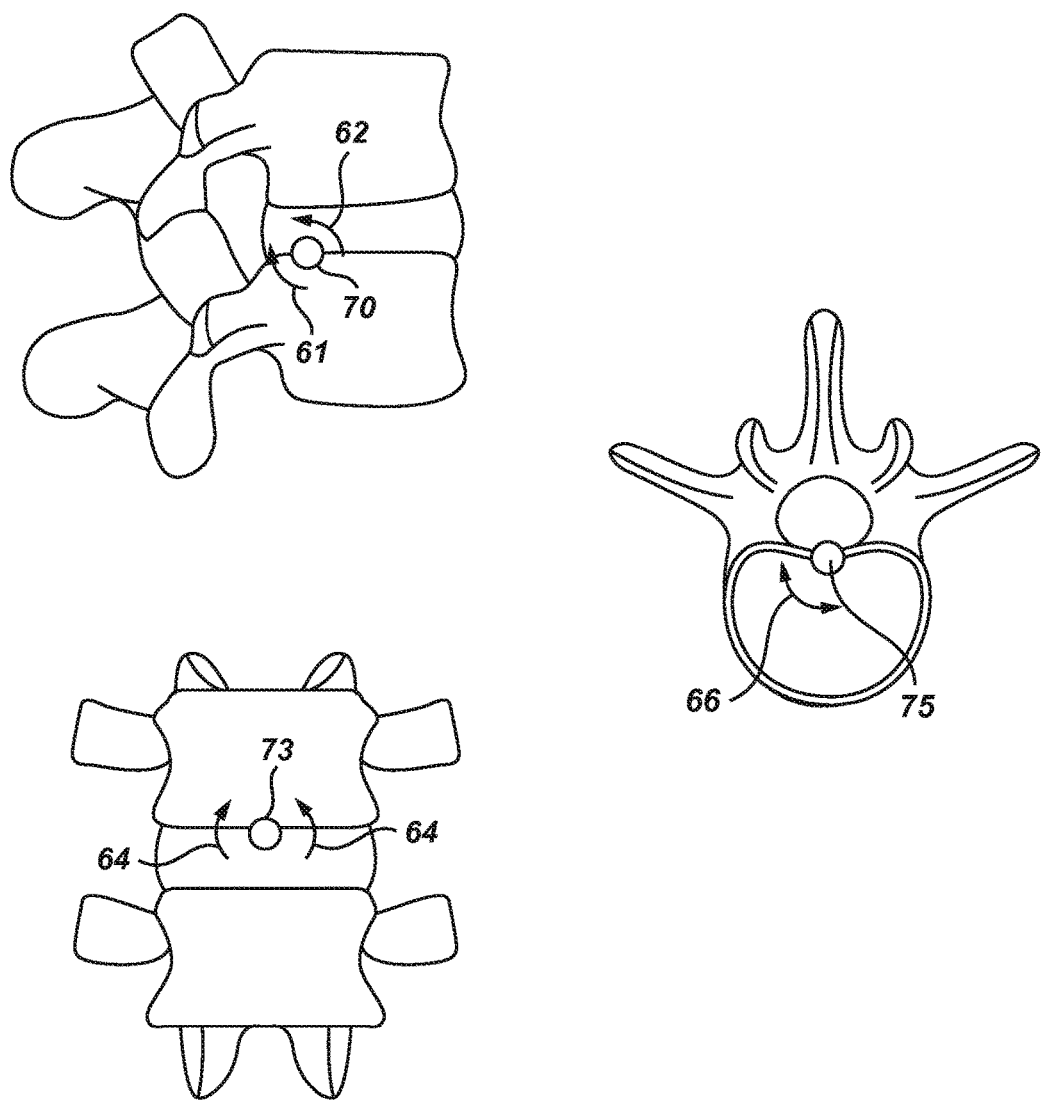
FIG. 7 illustrates the centers-of-motion of a functional spine unit.
Figure 12:
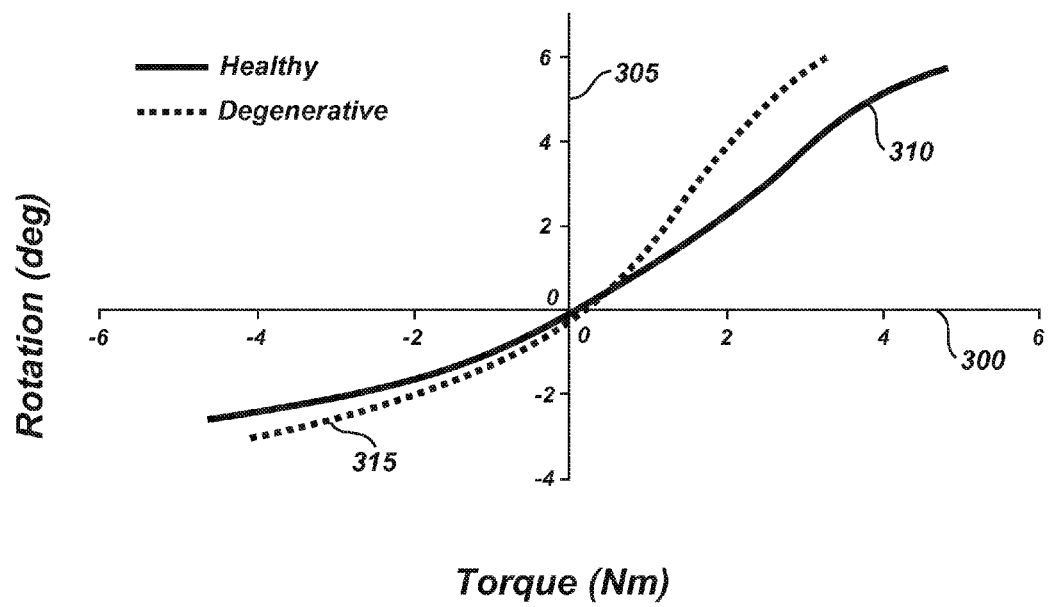
FIG. 12 is a graph of the rotation that occurs for a given torque for an exemplary healthy spine and an exemplary degenerative spine undergoing flexion and extension.
Figure 13:
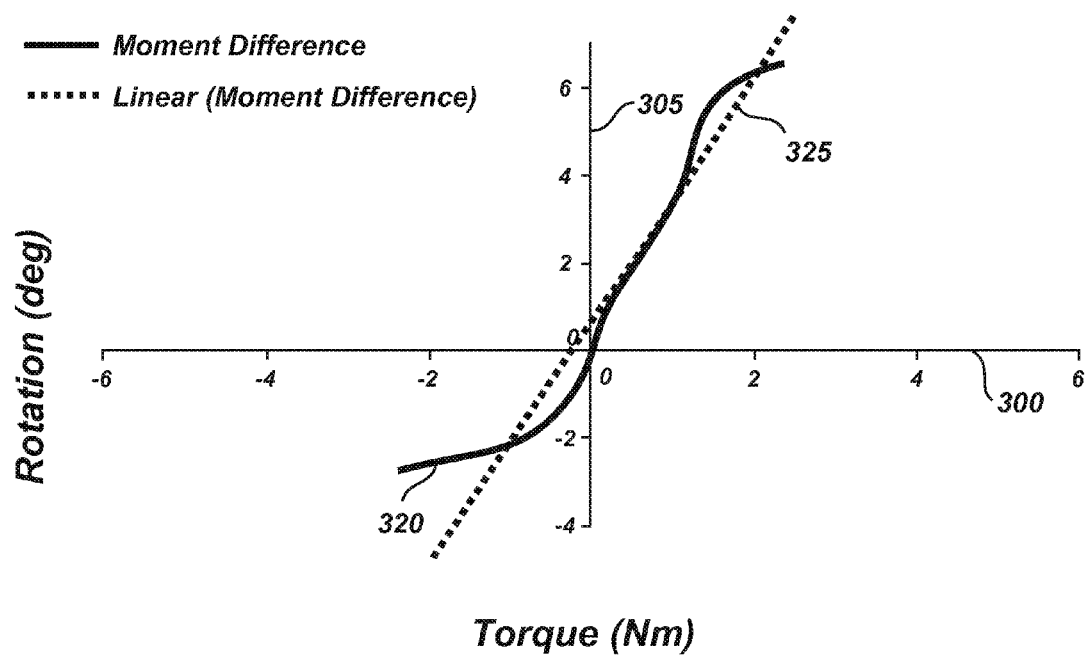
FIG. 13 is a graph of the moment difference between the response of the degenerative spine and the healthy spine graphed in FIG. 12 and a linear curve fit of the moment difference.
Figure 14:
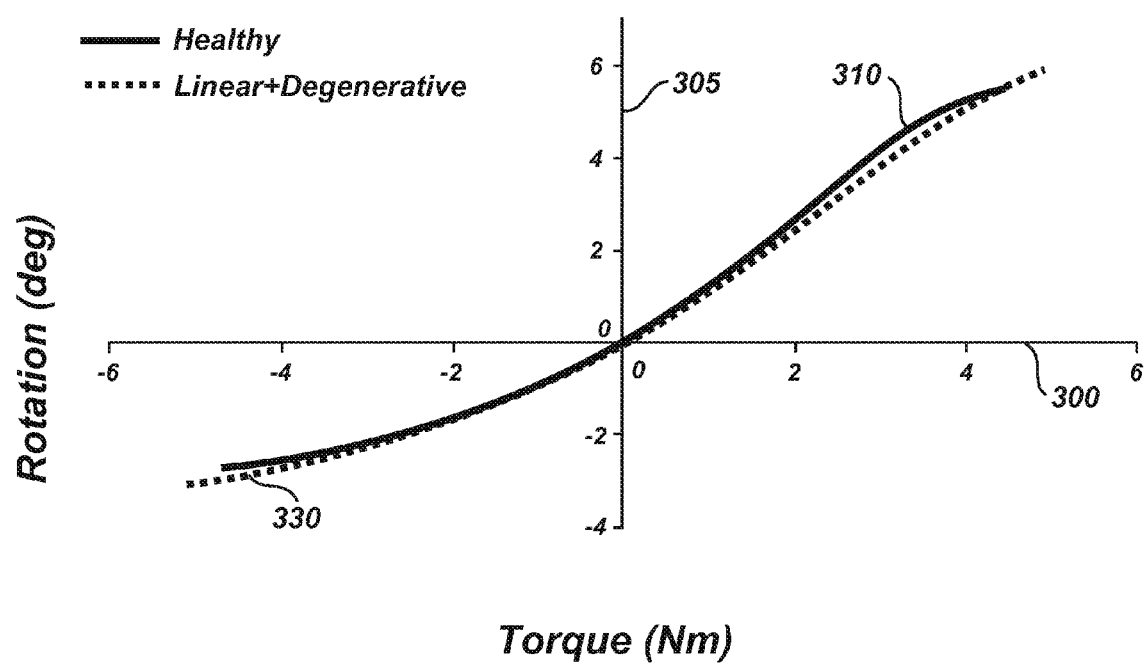
FIG. 14 is a graph of the healthy spine of FIG. 12 and the resultant rotation that occurs for a given torque of the degenerative spine (shown in FIG. 12) that has had an embodiment of the spinal implant that has been adjusted to exhibit a torque response that is the negative slope of the linear curve fit shown in FIG. 13.

Referring to FIGS. 12-14, an exemplary process for selecting and adjusting a spinal implant to a patient's pathology will be discussed. FIG. 12 is a graph of the torque-rotation response of a healthy and a diseased or degenerative disc undergoing flexion and extension, i.e., rotation in flexion 61 and extension 62 around the X-axis 60 as illustrated in FIG. 6 and corresponding to bending or leaning over and bending or leaning backwards. The X-axis 300 of the graph is the torque measured in Newton·meters (Nm). The Y-axis 305 of the graph is a measurement of the range of motion in rotation in degrees. The solid (healthy) curve 310 is the response of a healthy functional spine unit which, for example, can include the disc 208 illustrated in FIG. 11.

The dotted (degenerate) curve 315 is the response of a diseased or degenerative disc, such as disc 206 illustrated in FIG. 11. Qualitatively, FIG. 12 indicates that the diseased disc rotates more at lower torque than the healthy disc, indicating that there is a greater degree of laxity in the diseased disc, which may present as the disc bulging anteriorly and pressing against the spinal cord, causing pain, and/or other similar pathology. These measurements can be taken for the spine, as a whole, but, more preferably, the measurements are made at the vertebrae adjacent to the diseased disc. This is so because the torque-rotation response of the adjacent healthy vertebrae and discs should be the most similar to the response of the diseased disc when it was once healthy, a consideration since it is desired to restore the diseased disc to health.

Referring now to FIG. 13, this graph uses the same axes and scale as the graph in FIG. 12. In this instance, FIG. 13 plots the solid (moment difference) curve 320, which is the calculated difference in the response between the solid (healthy) curve 310 and the dotted (degenerate) curve 315 in FIG. 12. The dashed (linear) curve 325 is a linear curve fit of the solid (moment difference) curve 320.

A difference and improvement in the embodiments of the spinal implant disclosed herein is that the geometry of the spinal implant optionally uses this calculated moment difference as an input in the design process. The spinal implant 100 can, for example, be designed to provide a desired and known torque response when implanted in the patient as discussed above. In this example, the spinal implant 100 would have a linear torque-rotation response in flexion-extension that has a slope that is the negative of the dashed (linear) curve 325.

FIG. 14 illustrates the reason for creating a spinal implant that relies, in part, on the moment difference between the healthy disc and the diseased disc. Again, the same axes and scale are used in FIG. 14 as in FIG. 12. In this graph, the original solid (healthy) curve 310 is plotted. Now, however, a spinal implant designed and adjusted for the patient's pathology, has been implanted as described above. In other words, a spinal implant 100 is now supporting the diseased disc 206 and the adjacent vertebrae 204. As can be seen in FIG. 14, the spinal implant provides a desired stiffness, restoring the response of the dotted (degenerate) curve 315 to that of the dashed (linear and degenerate) curve 330 that is similar to the solid (healthy) curve 210. Qualitatively, it can be seen that with the spinal implant, the rotational response for a given torque is quite near that of the healthy disc.

While this example is provided for flexion and extension, one having skill in the art would understand that similar measurements can be made for lateral extension and axial rotation so that the results can be used, in part, as an input into the geometry of the spinal implant and, therefore, to allow the spinal implant to accommodate and support the motion of the spine in the three axes as discussed above. In brief, embodiments of the spinal implant can be designed and adjusted, in part, preoperatively for an individual patient's pathology. Embodiments of the spinal implant can restore, at least in part, a healthy torque-rotation signature to a diseased spine.

A further advantage of the above approach of measuring torque-rotation and similar data for use as an input is that it avoids a problem that appears in prior art devices. As briefly alluded to, many prior art devices have a limited range over which they function, typically force-displacement in compression and extension for the devices that commonly rely upon springs. These devices are not typically calibrated to an individual. As a result, it is not uncommon for these prior art devices to distract the diseased disc using an extension force that is too large for a given individual, causing undue strain on the surrounding muscles and ligaments, which may result in undue pain. In severe cases, the pain this causes might result in the patient unduly limiting his or her range of motion, resulting in nutritional deficiencies and other problems associated with minimal or a lack of movement in the spine and the disc, which was the outcome to be avoided initially.

Figure 15:
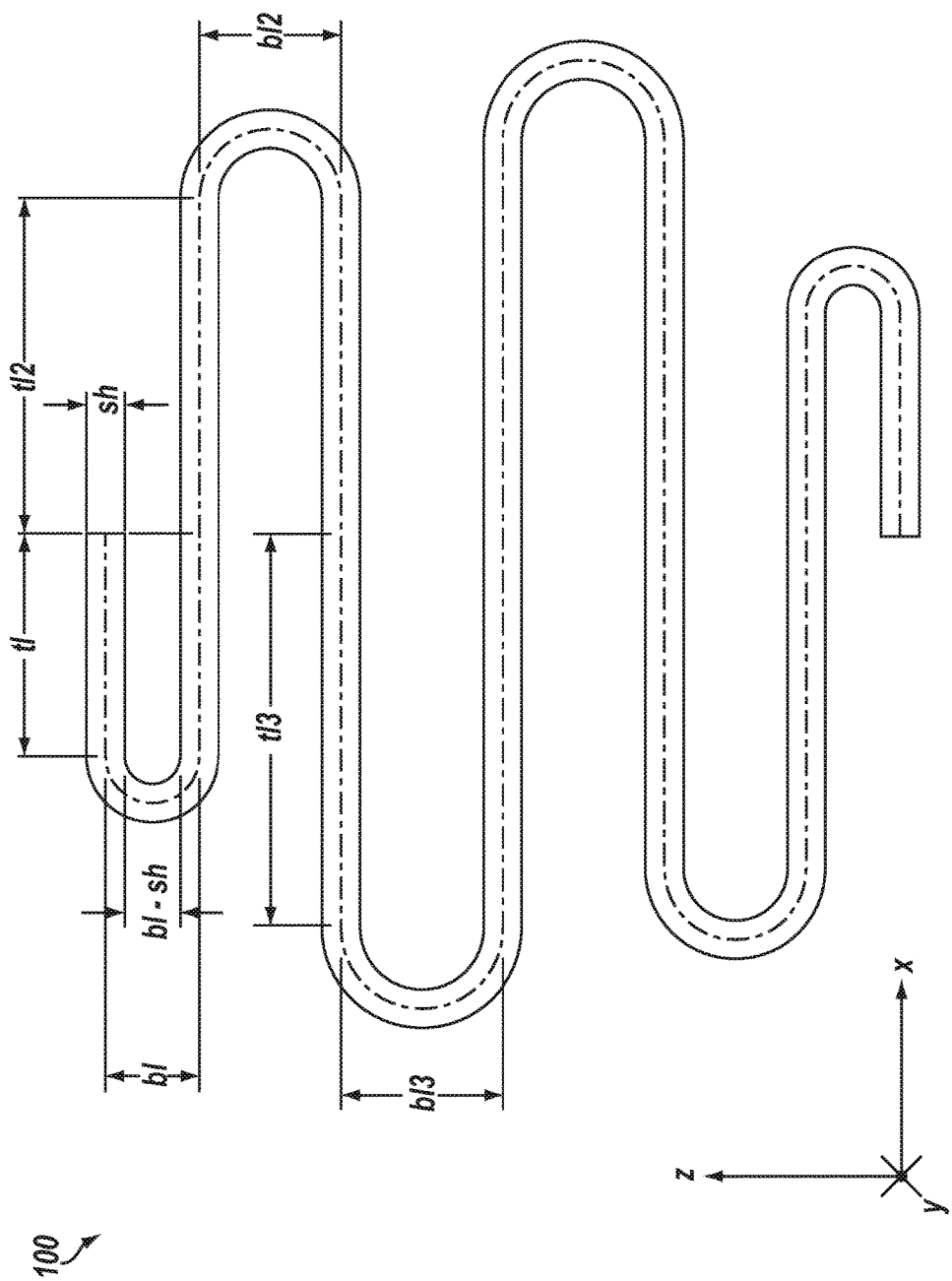
FIG. 15 is a schematic view of a generalized implant configuration in accordance with an embodiment of the invention.

FIG. 15 illustrates exemplary geometries of the implant 100 with the design variables defined (tl, tl2, tl3, bl, bl2, bl3 and sh). Note that, due to the symmetry of the device, the variables apply to both the top and bottom half of the device. An additional dimension, the width of the beams, is measured in the y direction of FIG. 15 (and shown at "W" in FIG. 8). The device was displacement loaded for an exemplary loading analysis.

Table I below illustrates exemplary design responses for differing objectives:

TABLE I

| Objective | 1 | 2 | 3a | 3b |
|---|---|---|---|---|
| Width | 4.88 mm | 12 mm | 15 mm | 18 m |
| sh | 0.55 mm | 0.91 mm | 1.29 mm | 1.45 mm |
| tl | 3.87 mm | 6.00 mm | 7.5 mm | 9.0 mm |
| tl2 | 3.24 mm | 6.00 mm | 7.5 mm | 9.0 mm |
| tl3 | 6.00 mm | 6.00 mm | 7.5 mm | 9.0 mm |
| bl | 2.09 mm | 1.58 mm | 1.95 mm | 2.12 mm |
| bl2 | 1.22 mm | 1.58 mm | 1.95 mm | 2.12 mm |
| bl3 | 4.19 mm | 4.40 mm | 3.59 mm | 3.46 mm |
| del | 0 mm | −0.1 mm | 0.0 mm | −0.37 mm |
| force | 0 N | 4.45 N | 4.35 N | 38.6 N |
| stress | 0 Pa | 21.0 MPa | 10.0 MPa | 68.8 MPa |
| force2 | 13.96 N | 93.4 N | 191.5 N | 246.2. N |
| stress2 | 422 Mpa | 440 MPa | 440 MPa | 440 MPa |

In this exemplary design optimization test, three objectives were targeted. Objective 1 had a target force (force2) of 14 N and minimized the geometric variables tl, tl2, tl3, bl, bl2, bl3, sh and width. Objective 2 maximized force for the previously mentioned geometric constraints. Objective 3 had two parts: 3a had a target pre-load force (force1) of 100 N and maximized force at the final deflection (force2), while maintaining the geometric constrains of 15 mm in x, 15 mm in y, and 15 mm in z. Objective 3b used the same pre-load force objectives as Objective 3a and maximized the final deflection force (force2) while maintaining the geometric constraints of 18 mm in x, 18 mm in y, and 15 mm in z.

The data show that the geometry of the implant can be much smaller than conventional units by utilizing the serpentine configuration, while still providing the same axial force-deflection profile. It was also shown that the serpentine design can attain very stiff force deflection characteristics, while fitting in the design restraints of 12 mm in x and y and being able to deflect the necessary 2 mm (again, compared to the limitations of a conventional device). If the geometric constraints are relaxed by 3 mm and 6 mm in the x and y direction while maintaining the geometric constraint in the z direction, a much stiffer device is possible, attaining up to 191.5 N at final deflection or 38.6 N of force at preload and 246.2 N of force at final deflection.

Figure 16A:
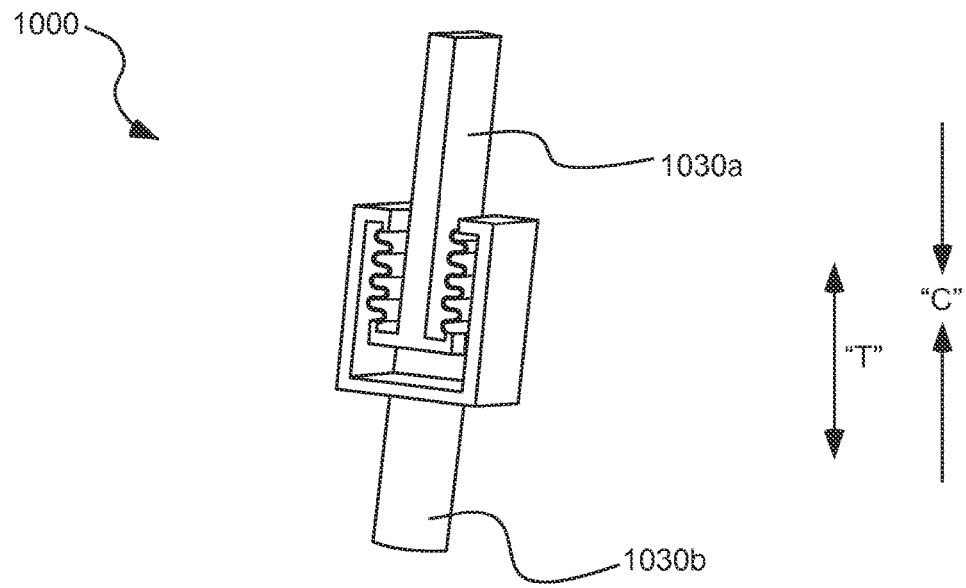
FIG. 16A is a graphical representation of an unimplanted compliant dynamic spinal implant in accordance with another embodiment of the invention.
Figure 16B:
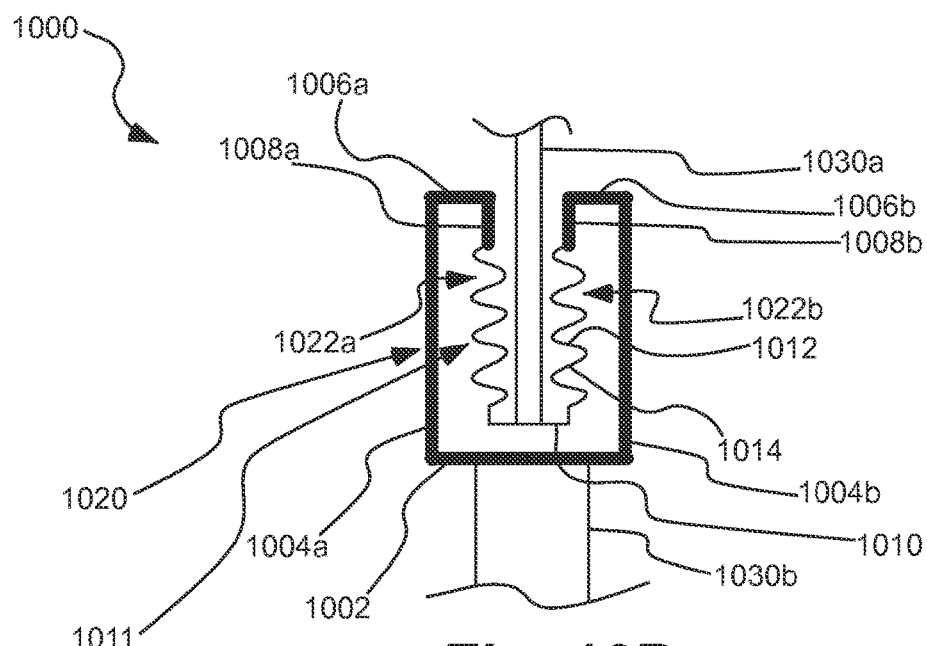
FIG. 16B is a schematic representation of the various components of the spinal implant of FIG. 16A.

Turning now to FIGS. 16A and 16B, another embodiment of the invention is illustrated: this embodiment incorporates many of the features and advantages of the previously discussed embodiments. In this aspect of the invention, the implant 1000 includes an "inverted" loading of the serpentine features discussed above. As the spine segment is placed into compression (shown by example at "C" in FIG. 16A), the serpentine segments of the spinal implant 1000 are placed into tension (shown by example at "T" in FIG. 16A).

As a compressive load is applied to the device 1000, the serpentine flexures experience tension. This design implementation is advantageous for many materials that have superior mechanical performance (e.g., increased material strength) in tension as compared to compression. This design can provide bilateral serpentine flexures, rather than a single serpentine flexure. In some embodiments, these bilateral flexures or arrays are positioned symmetrically about a centerline of the implant (e.g., they are spaced slightly to the left and right, respectively, of the center of the implant). This design implementation can be advantageous in tailoring the kinematic response of the device to provide a tailored stiffness along a curved path.

The inverted loading of the implant 1000 can provide additional range of motion for the device in compression. Some earlier embodiments experienced some limitations in that the adjacent levels of the serpentine flexure could come into contact under compression loading. The implant 1000 allows for additional flexibility in the sidewalls of the design, and for increased separability of the flexion-extension, lateral bending, and axial rotation stiffness, simplifying the tailorability of device design in each of these directions. The implant 1000 still allows for stiffness tailorability using a contact-aided insert (e.g., 120 in FIGS. 8 and 9)). This design also allows for included pre-load and pre-torque which can provide decompressive loading of the implanted spinal segment. A protective shroud (similar to that discussed above at 140) can also be implemented with this design.

As shown schematically in more detail in FIG. 16B, the implant 1000 can include a first, or outer frame 1020 that is coupled to mounting connection 1030b by way of lower frame segment 1002. A pair of outer frame segments 1004a, 1004b can extend upwardly from the lower frame segment. Inwardly extending upper segments 1006a, 1006b can extend toward coupling connection 1030a, then extend downwardly into segments 1008a, 1008b (without, generally, being directly attached to the mounting connection 1030a).

Segments 1008a, 1008b terminate at (or transition into) a series of serpentine segments, two of which, 1012 and 1014, are shown by way of example. A lower inner frame segment 1010 can be coupled directly to the mounting connection 1030a. These components form a second, or inner frame array 1011.

Thus, as a compressive load is applied to coupling connections 1030a and 1030b, those components will tend to move toward one another (in direction "C" shown in FIG. 16A). The serpentine segments (1012, 1014, etc.), however, will be placed into tension and thus the serpentine segments will tend to move away from one another (or "open" the serpentine spring). In this manner, the advantages outlined above can be achieved with a compact, reliable implant with long use cycle and relative ease of manufacture. This same result, only inverted, is achieved when a tensile load is applied to the first, outer frame segments. The second, inner frame array will thus experience a compressive load.

The two serpentine segments 1022a, 1022b shown can be individually tailored to provide differing force response. For example, an overall shape, or the material from which the segments are formed can be varied, a depth (into the page of FIG. 16B) can be varied, a thickness of the ribbon can be varied, a width (across the page of FIG. 16B), a length, etc. In this manner, the implant 1000 can provide varying loading characteristics, as may be appropriate to a particular patient or condition. Each of the serpentine segments can be adjusted to provide a similar loading response, or they can provide differing loading responses.

In one embodiment of the invention, the first, outer frame array 1020 can substantially circumvent the second frame array 1011. This can provide a compact, easily implantable device. Each of the first and second frame arrays can include a depth (into the page of FIG. 16B). In one embodiment, these depths are substantially equal. In other embodiments, the depth of the inner frame array is no more than a depth of the outer frame array (to prevent the inner frame array from protruding beyond the outer frame array). Regardless of the magnitude of these depths, they can be substantially constant from an upper portion of the implant (near segment 1006a, for example) to a lower portion of the implant (near segment 1002, for example).

Figure 4:
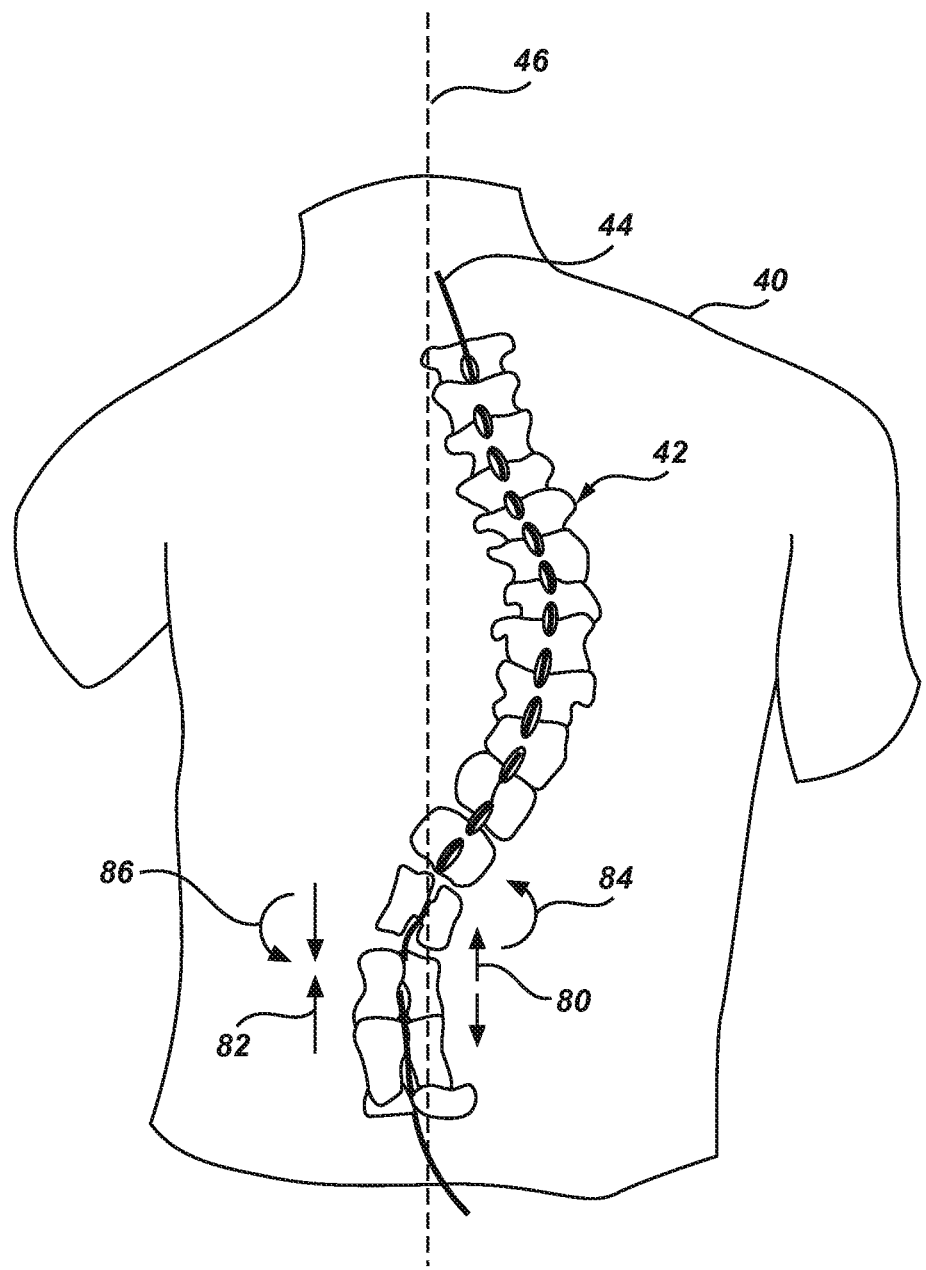
FIG. 4 is a scoliotic spine.

Embodiments of the spinal implant disclosed herein provide additional benefits, such as:

Treating Scoliosis, Kyphosis, Lordosis, and/or Similar Pathologies: For example, with reference to FIG. 4 which illustrates a spine presenting with scoliosis, embodiments of the disclosed spinal implant can treat the scoliosis. This is done by using spinal implants that have different torque-rotation signatures from each other. That is, rather than using spinal implants 100 having the same torque-rotation signature as illustrated in FIG. 10, in the instance of scoliosis one of the spinal implants would have a different and, possibly, opposite, torque-rotation signature than the other. In addition, a prestressed force may be applied to one or both of the spinal implants so that they apply a force to one or both sides of the scoliotic spine. In other words, the torque and/or any force applied by the spinal implants would be unbalanced in order to counteract the curvature of the scoliotic spine. For example, in FIG. 4 an extensive force 82 can be applied on the right side of the lumbar area of the spine by one spinal implant, while on the left side another spinal implant could apply a compressive force on the left side of the lumbar area of the spine, tending to cause the lumbar spine to straighten. Alternatively, or in addition to, the unbalanced forces, torques 84 and 86 could be applied to the spine by the spinal implants. A similar strategy could be used to treat other conditions of the spine that present similar pathology to scoliosis, such as kyphosis, lordosis, and the like.

Figure 5:
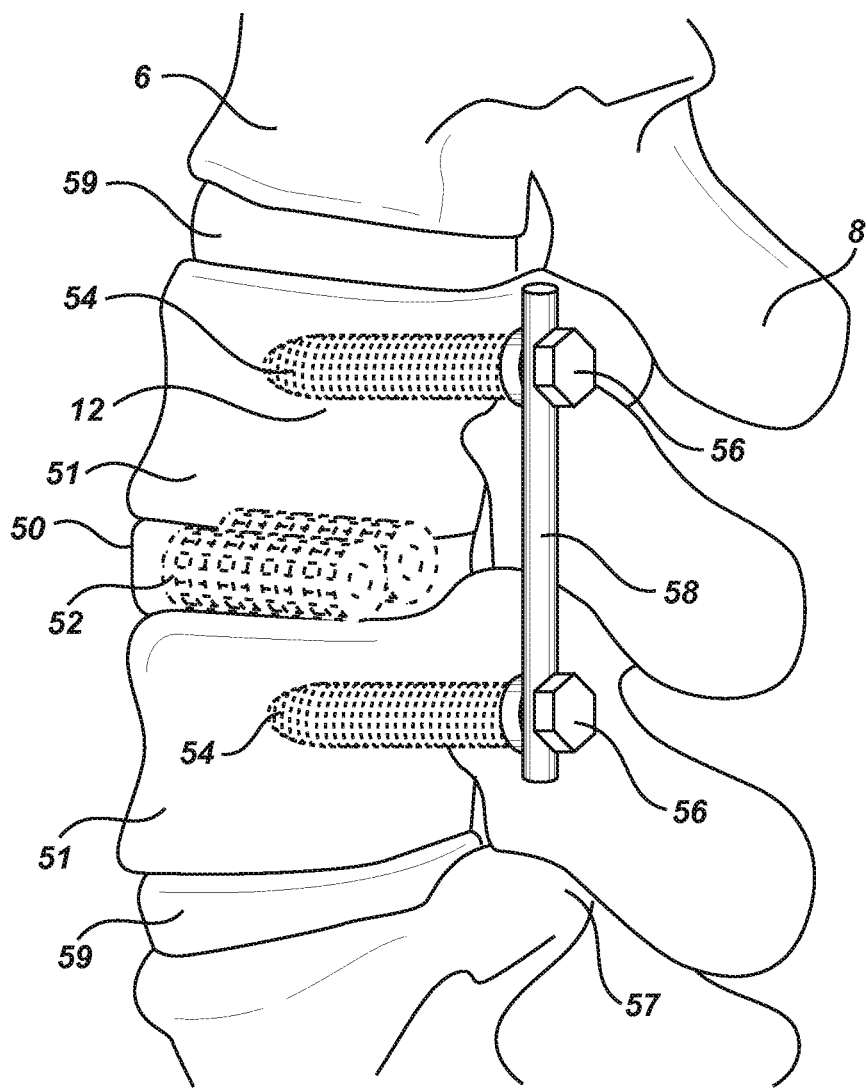
FIG. 5 is a prior art discectomy and spinal fusion.

Provide Distraction of the Vertebrae to Allow Healing of the Diseased Disc:

As noted, a spinal implant can be prestressed to provide a torque and/or extensive force to distract, either anteriorly, posteriorly, or both, the portion the vertebrae adjacent to a diseased disc. In so doing, the spinal implants carry or bear a portion of the force normally borne by the diseased disc, as well as an additional force that static devices such as the prior art posterior support 58 in FIG. 5 do not carry. This arrangement allows sufficient support and space for the diseased disc to heal while still providing for sufficient moment that static prior art devices and procedures (such as spinal fusion) do not provide. In other words, embodiments of the spinal implant provide an opportunity for the diseased disc to heal, which may allow the spinal implants to eventually be removed.

Protect Spinal Cord and Periphery Nerves: The embodiments disclosed provide, in part, a measure of protection to the spinal cord and peripheral nerves from being impinged by bulging and/or herniated discs and/or parts of the skeletal structure and other parts of the anatomy afflicted with various pathologies as described above.

Limit Range of Motion and Provide Stiffness: The embodiments disclosed, as shown graphically in FIGS. 12-14, restore a measure of stiffness and limit the range of motion that might otherwise be causing pain, such as through muscles overexerting themselves to compensate for the laxity caused by a diseased disc. By limiting the range of motion, the strain on muscles and ligaments is reduced, thereby reducing risk of injury to those muscles. Further, laxity is reduced, thereby improving the structural stiffness (as opposed to the colloquial muscle stiffness caused by over-exertion) of the spine.

Kinetics Similar to a Healthy Spine: Related to limiting the range of motion discussed above, the motion that embodiments of the spinal implant provide in the three axes discussed above regarding FIG. 6 is similar to that of a healthy spine. What this provides is that the patient's muscles and ligaments do not have to compensate for an unnatural motion of the spinal implant, unlike the case with prior art devices. In other words, the spinal implant provides more natural motion, which would encourage patients to move more with less attendant pain as their muscles would not be compensating or overworking for a prior art spinal implant that does not provide such natural motion around all three axes. In so doing, the movement provides further nutrition to the discs, increasing the likelihood that the discs will heal.

Kinematics Similar to a Healthy Spine: Related to the kinetics are the natural kinematics of embodiments of the spinal implants. As discussed above, the centers-of-rotation for flexion-extension, lateral extension/bending, and axial rotation, are each located in different places. Prior art devices could not accommodate these separate centers-of-rotation around more than one axis, if even that, nor could they provide for the instantaneous or near instantaneous change in the location of the centers-of-motion as a spinal segment moves, nor could they provide for motion approximate the motion of a natural helical axis. Stated differently, the center-of-rotation of prior art devices often was in a different location than the natural center-of-rotation of the spine for a given movement. To compensate, patients with prior art devices suffered strain upon the spinal cord and peripheral nerves, muscle strain caused by the muscles overworking and compensating for the two different centers-of-rotation (that of the prior art device and that of the spine), ligament strain, and, consequently, pain. In contrast, embodiments of the present spinal implant provide centers-of-rotation in each of the three axes that is the same, or nearly the same, as a patient's natural centers-of-rotation for the spine. Thus, patients typically have less pain and, consequently, greater movement, to the benefit of the discs and the spine in general.

Adjust to the Individual Spine: As noted, embodiments of the spinal implant can be designed and/or selected preoperatively for an individual patient's torque-rotation response in order to provide implants that restore the diseased disc/spine to near healthy function. Related to this is the ability to prestress embodiments of the implant prior to, or even during, surgery to allow the surgeon to further individually tailor the torque-rotation response of the spinal implant to the individual patient as determined at the time.

Further, embodiments of the spinal implant are adjustable post-surgically. As noted, spinal implants made of bioabsorbable material will gradually degrade and, in the process, transfer ever greater portions of the force and torque once borne by the spinal implant back to the patient's spine as it heals. A further benefit of this is that these embodiments do not need to then be surgically removed, reducing cost and risks to the patient. Alternatively, embodiments of the spinal implant can be made from shape-memory materials, such as nitinol. The use of shape memory materials allows the spinal implant to be configured in a second geometry or shape upon surgical implantation and then, upon application of some transformation parameter, such as heat, the spinal implant reverts to a first geometry or shape with different mechanical properties (such as stiffness and/or torque), thus allowing a physician to subsequently alter the treatment of the patient without surgical intervention.

Reduced Wear: As noted, embodiments of the spinal implant do not have moving components or components that rub against one another, thereby reducing or eliminating the generation of wear particles. Further, because embodiments of the spinal implant rely upon torsion and/or torsion beams rather than compression and extension that springs and other similar devices rely upon, reduces or eliminates the risk of the material from which the spinal implant is made suffers from fatigue and/or fatigue failure, thereby increasing the reliability of the spinal implant.

Thus, disclosed above, in addition to the embodiments of the spinal implant are methods of treating a spine with a spinal implant configured to provide motion in three axes; methods of treating a spine with a spinal implant that provides kinetics and kinematics similar to that of a functional spine; methods of treating pathologies that cause the spine to curve; methods of healing a diseased or degenerated disc; methods of adjusting a spinal implant without surgical intervention; methods of reducing the wear of a spinal implant; methods of providing a near healthy torque-rotation signature to a degenerate spine; and other methods as will be recognized by one of skill in the art.

As alluded to above, embodiments of the spinal implant are surgically implanted. While the spinal implants disclosed herein can be implanted using either an anterior, posterior, or lateral incision in the patient, a preferred method is to use a posterior incision. Further, it is preferred that a minimally invasive procedure be used, such as by laparoscopy in which only one or a few, small incisions are made and the surgery is conducted with laparoscopic tools. The methods include making an incision; providing an embodiment of the spinal implant disclosed herein; using a positioning tool to position the spinal implant and counter and prestress designed into the spinal implant; and fixing the spinal implant to two adjacent vertebrae. The surgical procedure does not require that the disc space be distracted extensively to install the spinal implant, thereby reducing the pain and recovery time endured by the patient. The method optionally includes implanting spinal implants with different characteristics, such as different prestressed torques, for treating pathologies such as scoliosis. Fixing the spinal implant to the vertebrae may be done by applying straps, applying biocompatible adhesives, installing pedicle screws, and the like, as known in the art.

Alternative methods and positions of placing the spinal implant include locating them on the anterior side of the spine rather than the posterior side. Spinal implants positioned to the anterior side can be reached through an incision in the patient's back and positioned between the transverse process of adjacent vertebral bodies or mechanically attached to the anterior portion of the vertebral body.

The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A spinal implant comprising:
   a plurality of frame segments that define a first frame array, said first frame array being coupled to a first mounting connection; and
   a plurality of contiguous segments that define a second frame array, said plurality of contiguous segments being coupled to a second mounting connection and being coupled to the first frame array;
   the first frame array and the second frame array being positioned relative to one another such that application of a force in a first direction to the first and second mounting connections results in application of a force in an opposing direction to the plurality of contiguous segments.

2. The implant of claim 1, wherein application of a compressive force to the first and second mounting connections results in application of a tensile force to the plurality of contiguous segments.

3. The implant of claim 1, wherein application of a tensile force to the first and second mounting connections results in application of a compressive force to the plurality of contiguous segments.

4. The spinal implant of claim 1, wherein each of said plurality of contiguous segments is joined by a continuously curving end segment that transitions from one segment to an adjacent, overlapping segment.

5. The spinal implant of claim 1, wherein the array of contiguous segments is formed from a ribbon of material that alternately and contiguously extends from one side of the array to another side of the array in an overlapping configuration.

6. The spinal implant of claim 1, wherein the array includes at least four overlapping segments.

7. The spinal implant of claim 1, wherein the array of contiguous segments includes a pair of arrays, arranged in a substantially parallel arrangement.

8. The spinal implant of claim 7, wherein the pair of arrays are positioned symmetrically adjacent a longitudinal axis of the implant.

9. The spinal implant of claim 7, wherein the pair of arrays differ in one of a: size, shape, thickness, depth or material, such that one array of the pair of arrays produces a differing force reaction than another array of the pair of arrays.

10. The spinal implant of claim 1, further comprising a protective shroud, fittable about the spinal implant, the protective shroud configured to limit surrounding tissue from contacting the spinal implant.

11. The spinal implant of claim 10, wherein the protective shroud is coupleable to the insert.

12. The spinal implant of claim 1, wherein the second frame array is circumvented by the first frame array.

13. The spinal implant of claim 1, wherein the first frame array includes a depth, and the second frame array includes a depth not greater than the depth of the first frame array.

14. The spinal implant of claim 13, wherein depths of the first frame array and the second frame array are substantially constant from an upper portion of each array to a lower portion of each array.

* * * * *